United States Patent
Choi

(10) Patent No.: US 10,493,004 B2
(45) Date of Patent: Dec. 3, 2019

(54) COSMETIC COMPOSITION CARRIER COMPRISING INTEGRATED SPONGE HAVING LAYERED STRUCTURE

(71) Applicant: AMOREPACIFIC CORPORATION, Seoul (KR)

(72) Inventor: Jung Sun Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/564,592

(22) PCT Filed: Apr. 6, 2016

(86) PCT No.: PCT/KR2016/003564
§ 371 (c)(1),
(2) Date: Oct. 5, 2017

(87) PCT Pub. No.: WO2016/163730
PCT Pub. Date: Oct. 13, 2016

(65) Prior Publication Data
US 2018/0071176 A1  Mar. 15, 2018

(30) Foreign Application Priority Data
Apr. 8, 2015 (KR) .................. 10-2015-0049839

(51) Int. Cl.
| | |
|---|---|
| A61K 8/02 | (2006.01) |
| A61K 8/06 | (2006.01) |
| A61Q 1/00 | (2006.01) |
| A61Q 19/00 | (2006.01) |
| A45D 34/00 | (2006.01) |

(52) U.S. Cl.
CPC ............ *A61K 8/0208* (2013.01); *A45D 34/00* (2013.01); *A61K 8/062* (2013.01); *A61K 8/064* (2013.01); *A61Q 1/00* (2013.01); *A61Q 19/00* (2013.01); *A45D 2034/007* (2013.01); *A45D 2200/1036* (2013.01)

(58) Field of Classification Search
None
See application file for complete search history.

(56) References Cited

U.S. PATENT DOCUMENTS 2,865,283 A    12/1958  Stoffer
9,492,370 B2 *  11/2016  Choi .................... A61K 8/0204

FOREIGN PATENT DOCUMENTS

| EP | 2468235 A1 | 6/2012 |
|---|---|---|
| JP | 3187673 B2 | 5/2001 |
| JP | 2003231197 A | 8/2003 |
| KR | 1020090100643 | 9/2009 |
| KR | 101351769 * | 1/2014 |
| KR | 101351769 B1 | 1/2014 |
| WO | 0121501 A1 | 3/2001 |
| WO | 2017078204 A1 | 5/2017 |

OTHER PUBLICATIONS

Extended European Search Report dated Oct. 19, 2018, in reference to application No. 16776833.2.
International Search report for PCT/KR2016/003564, dated Jun. 8, 2016 (4 pages).

* cited by examiner

*Primary Examiner* — Robert A Wax
*Assistant Examiner* — Danah Al-Awadi
(74) *Attorney, Agent, or Firm* — Cantor Colburn LLP

(57) ABSTRACT

The present invention provides: a cosmetic composition carrier comprising an integrated sponge having a layered structure; and a cosmetic product comprising the same. According to the present invention, the cosmetic composition carrier facilitates the filling of a cosmetic composition, can uniformly carry the cosmetic composition for a long time, discharges an appropriate amount of the cosmetic composition when using the cosmetic composition, and can maintain excellent durability for a long time even after the cosmetic composition is carried.

12 Claims, 2 Drawing Sheets

COSMETIC COMPOSITION CARRIER COMPRISING INTEGRATED SPONGE HAVING LAYERED STRUCTURE

TECHNICAL FIELD

The present disclosure relates to a carrier for a cosmetic composition by which the cosmetic composition is supported.

BACKGROUND ART

In general, liquid cosmetic compositions have been packed, distributed and stored in a vacuum container, pump container or glass container. However, such containers have low portability. Recently, there has been an increasing need for carrying out or correcting make-up with ease even at the outdoor, and thus an easily portable liquid cosmetic composition has been required.

Containers that allow high portability of a liquid cosmetic composition may include a pact type container. It is required to consider whether or not a carrier for a liquid cosmetic composition can be used for a pact type container, whether or not the cosmetic composition can be packed well in the carrier, whether or not the carrier can support the cosmetic composition homogeneously for a long time, and whether or not an adequate amount of cosmetic composition can be discharged when the cosmetic composition is taken out of the carrier, in order for a pact type container to receive a liquid cosmetic composition. Thus, there is a need for developing a carrier for a cosmetic composition that may be used suitably for a pact type container, considering the above.

When a single carrier is formed by coupling a plurality of layers, at least two foam layers are adhered, and thus some problems related with safety, heat resistance and weather resistance may occur. Therefore, the present disclosure is directed to solving the problems according to the related art, while maintaining the effects as multi-layered carrier.

REFERENCES

Patent Document (Patent Document 1) Korean Patent Publication No. 10-2009-0100643

DISCLOSURE

Technical Problem

A technical problem to be solved by the present disclosure is to provide a carrier for a cosmetic composition which has a single-body shape while maintaining a layered structure so that a cosmetic composition may be packed well therein, supports a cosmetic composition homogeneously for a long time, allows discharge of an adequate amount of cosmetic composition when the cosmetic composition is taken out of the carrier, and avoids a need for interlayer binding so that excellent durability may be retained even after the cosmetic composition is supported, as well as a cosmetic product including the same.

Technical Solution

In one general aspect, there is provided a carrier for a cosmetic composition including a single-body type sponge having at least two layers. According to an embodiment, the layers of sponge may be different from each other in at least one of sponge density, pore number per unit volume (1 $cm^3$), pore size and layer thickness.

According to another embodiment, the single-body type sponge may include pores and may have a layer controlled in at least one of density, pore number per unit volume (1 $cm^3$), pore size and layer thickness through pressurization of a part of the single-body type sponge.

According to still another embodiment, the pressurization may be carried out by pressing, melting or felting.

According to still another embodiment, the pressurized layer in the layers of single-body type sponge may have a density of 0.025-0.5 $g/cm^3$.

According to still another embodiment, the pore number per unit volume (1 $cm^3$) of the single-body type sponge may be 1000-600,000.

According to still another embodiment, the number of pores contained per unit inch (1 inch) of the single-body type sponge may be 30 ppi-130 ppi (pore per inch).

According to still another embodiment, the pore size of the single-body type sponge before pressurization may be 100-1500 μm on average.

According to still another embodiment, the pressurized layer in the single-body type sponge may have a thickness corresponding to 0.5-60% based on the total thickness of the single-body type sponge.

According to still another embodiment, the single-body type sponge may have a network structure.

According to yet another embodiment, the single-body type sponge may have a surface pattern formed thereon.

In another aspect, there is provided a cosmetic product, including: the carrier for a cosmetic composition; and a cosmetic composition supported by the carrier.

According to an embodiment, the cosmetic composition may include a liquid composition.

According to another embodiment, the cosmetic composition may include at least one of an emulsion composition, water in oil (W/O) type composition or oil in water (O/W) type composition, oil dispersed composition, water dispersed composition and a solubilized composition.

Advantageous Effects

According to the embodiments of the present disclosure, the carrier for a cosmetic composition includes a single-body type sponge having a plurality of layers different from each other in density, pore number per unit volume, pore size and layer thickness. Thus, the carrier for a cosmetic composition allows easy packing of a cosmetic composition, supports a cosmetic composition homogeneously for a long time, allows discharge of an adequate amount of cosmetic composition when the cosmetic composition is taken out of the carrier, and retains high durability for a long time even after supporting a cosmetic composition.

BEST MODE

Figure 1:
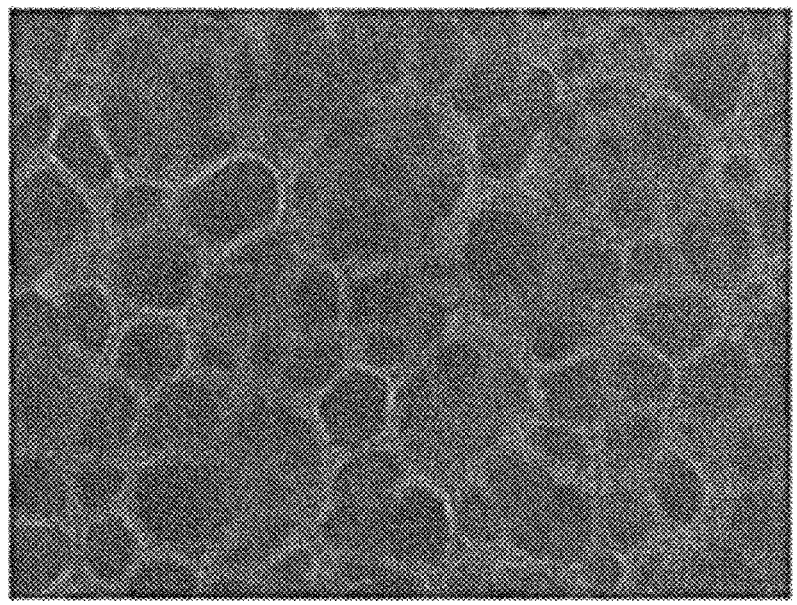
FIG. 1 is a microscopic image of the surface pores (85 ppi) of the conventional carrier according to Comparative Example.
Figure 2:
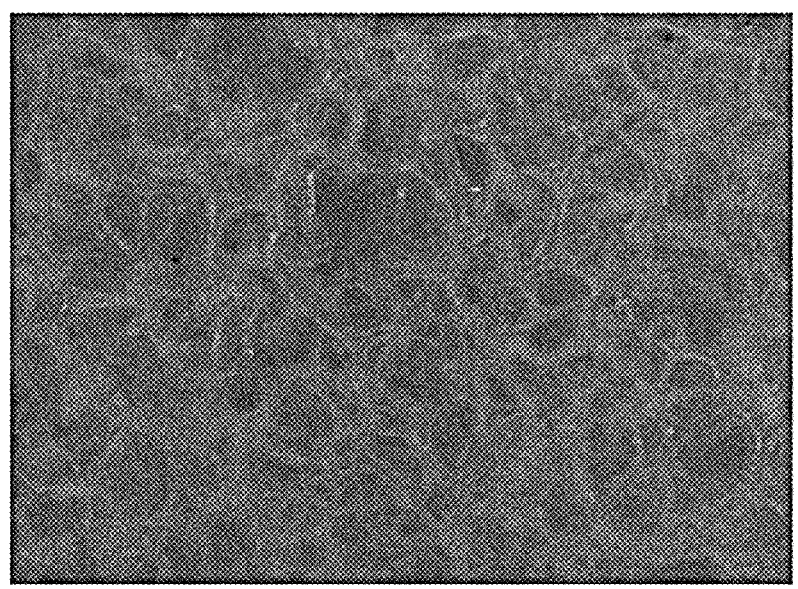
FIG. 2 is a microscopic image of the hot pressurized surface pores (85 ppi) of the single-body type carrier for a cosmetic composition according to an embodiment of the present disclosure.

Hereinafter, specific exemplary embodiments of the present disclosure are described in detail such that those of ordinary skill in the art to which the present disclosure belongs can easily carry out the present disclosure.

In one aspect, there is provided a carrier for a cosmetic composition which includes a layered structure having at least two layers. The carrier for a cosmetic composition may have a layered structure including at least two layers, particularly 2-20 layers, more particularly 2-10 layers, and even more particularly 2-5 layers.

As used herein, the term 'carrier' means one capable of supporting any material, such as a composition, or any ingredient, and is used interchangeably with 'carrier body' or 'medium'. In addition, 'carrier' may be one used in such a manner that the material supported thereby may be discharged to a separate applicator. As used herein, the term 'supportability' means the ability of receiving and retaining any material or ingredient. The supportability required for a carrier is differentiated from taking a material temporarily on an applicator in that a composition is supported homogeneously for a long time.

As used herein, the term 'packability' or 'packing capability' means the ability of packing a cosmetic composition by a carrier, and may be expressed in terms of time required for packing a predetermined amount of cosmetic composition in a carrier.

As used herein, the term 'dischargeability' or 'discharge capability' means an amount of cosmetic composition discharged when the cosmetic composition is taken out of the carrier supporting the same by using an applicator. It is preferred that an adequate amount of cosmetic composition is discharged, no more and no less than that.

As used herein, the term 'durability' means how much the sponge included in a carrier retains its state without melting, tearing or swelling when a cosmetic composition is supported by the carrier and allowed to stand at a predetermined temperature for a predetermined time and/or how much the carrier resists repeated pressure applied by an applicator when a cosmetic composition is taken out of the carrier with the applicator during use.

As used herein, the term 'sponge' means a material capable of supporting any material, such as a composition, or any ingredient, includes rubber, fibers or resin formed in the form like sponge, and covers one capable of supporting and discharging a cosmetic composition. Particularly, the sponge may be natural sponge or synthetic sponge but is not limited thereto. For example, the natural sponge may be bath sponge, natural rubber sponge, or the like. And, the synthetic sponge may be exemplified by synthetic resin sponge, urethane, foamed urethane, latex, acrylonitrile-butadiene rubber (NBR), butadiene rubber (BR), styrene-butadiene rubber (SBR), natural rubber (NR), chloroprene rubber (CR), butyl rubber (isoprene-isobutylene rubber: IIR), isoprene rubber (IR), vulcanized ethylene-propylene rubber (EPR), polysulfide rubber, silicone rubber, fluororubber, urethane rubber, acrylic rubber, ethylene propylene diene monomer (EPDM) rubber, polyvinyl alcohol (PVA), ethylene vinyl acetate (EVA), nitrile rubber (NR), or the like.

As used herein, the term 'foamed urethane' means foamed and solidified polyurethane, and is used interchangeably with 'urethane foam'. According to an embodiment, the foamed urethane may be exemplified by polyether-based foamed urethane, polyester-based polyurethane or polycarbonate-based polyurethane, but is not limited thereto.

As used herein, the top layer of the layers of sponge means a layer to be in contact with an applicator (or application means), such as a hand, puff, tip or brush, or a layer adjacent to the same. Particularly, the topmost layer means a layer to be in direct contact with an applicator. In addition, the bottom layer means a layer opposite to the side to be in contact with an applicator (or application means), such as a hand, puff, tip or brush. Particularly, the bottommost layer means the lowest layer of such opposite layers.

The layers of sponge may be different from each other in at least one of sponge density, pore number per unit volume (1 $cm^3$), pore size and layer thickness. Otherwise, the layers of sponge may be formed by pressurizing, compressing or melting a part of one sponge so that at least one of density, pore number, pore size and layer thickness may be controlled.

Herein, the pressurizing, compression or melting may be carried out by pressing, melting or felting, but is not limited thereto. As used herein, the term 'pore number' means a number of pores per inch (ppi) or pore number per unit volume (1 $cm^3$) according to the calculation base. When a sponge is pressurized, the number of linear pores per inch is constant with no change. However, the pore number per unit volume increases so that the sponge may have improved absorption and supporting capability to a cosmetic composition and may be controlled in such a manner that the cosmetic composition is discharged finely.

According to an embodiment, the carrier for a cosmetic composition disclosed herein does not include a plurality of sponge parts bound or sealed with ultrasonic waves, heat, a binder or adhesive, but includes a single-body type sponge a part of which is pressurized by pressing, melting or felting so that the sponge may have a multilayered structure. There is no particular limitation in the portion to be pressurized, as long as it requires pressurization, and the portion may be at least one of the top layer, intermediate layers, bottom layer and lateral surfaces of the sponge. For example, the sponge may be pressurized both at the topmost layer and the bottommost layer thereof. Therefore, it is possible to avoid a problem related with safety to the human body, shape stability, applicability and durability, which, otherwise, may occur due to the sealing using ultrasonic waves, heat, a binder or adhesive.

Particularly, in the case of a conventional carrier having a layered structure formed by binding or sealing of a plurality of sponge parts using ultrasonic waves, heat, a binder or adhesive, interlayer separation may be observed during a stability test, including adhesion stability at high temperature, adhesion stability in boiling water, adhesion stability against materials, and adhesion stability against physical force. In addition, in the case of such a conventional carrier, some harmful materials may be detected due to an adhesive, or safety against adhesion application should be ensured in a safety test, including a harmful material test and safety test. Further, in an applicability test, such a conventional carrier may undergo degradation of discharge capability due to the interlayer film formation caused by the use of an adhesive. On the contrary, the single-body type sponge according to the present disclosure requires no interlayer sealing (integration), and thus the above-mentioned problems are not under consideration in the case of the single-body type sponge.

According to an embodiment, the single-body type sponge, before pressurization, may have a density of 0.01-

0.2 g/cm³ (0.624-12.486 lb/ft³), particularly 0.1-0.18 g/cm³ (6.24-11.23 lb/ft³), for example, 0.01 g/cm³ or more, 0.05 g/cm³ or more, 0.10 g/cm³ or more, 0.15 g/cm³ or more, or 0.2 g/cm³ or less, 0.15 g/cm³ or less, 0.1 g/cm³ or less, 0.05 g/cm³ or less. When the sponge has a density less than 0.01 g/cm³ before pressurization, it discharges an excessively large amount of cosmetic composition, and thus is not convenient to use. When the sponge has a density larger than 0.2 g/cm³ before pressurization, it may not support/discharge a cosmetic composition well.

As defined herein, density may be a value determined by the method of ASTM (American Standard Test Method) D3574. ASTM D3574 is a method for determining physical properties of a foam-like material, such as the sponge disclosed herein. It is possible to determine the unit volume and weight of a material by using the method, and thus to calculate the density. When determination is carried out by using the method, the unit volume of a material should be 1000 mm³ or more and the weight for a unit volume of 6 inch³ is determined.

According to an embodiment, the pressurized layer of the single-body type sponge, i.e., the layer having a high density among the multiple layers of the single-body type sponge may have an average density of 0.025-0.5 g/cm³. When the sponge has a density less than 0.025 g/cm³ after pressurization, there is no difference in discharge capability. When the sponge has a density larger than 0.5 g/cm³, it has excessively high density, resulting in degradation of discharge capability.

In other words, the layers of the single-body type sponge disclosed herein may have a different density. In addition, the lower-density layer may have a density of 0.01-0.2 g/cm³ and the higher-density layer density may have a density of 0.025-0.5 g/cm³.

According to an embodiment, the pore number of single-body type sponge may be 1,000-600,000 per unit volume (1 cm³), particularly 1,500-500,000.

According to another embodiment, the pore number per inch of the single-body type sponge may be 30 ppi-130 ppi (pore per inch), particularly 50 ppi-120 ppi, and more particularly 60 ppi-110 ppi. For example, the pore number per inch may be 30 ppi or more, 40 ppi or more, 50 ppi or more, 60 ppi or more, 70 ppi or more, 80 ppi or more, 90 ppi or more, 100 ppi or more, 110 ppi or more, 120 ppi or more, or 130 ppi or less, 120 ppi or less, 110 ppi or less, 100 ppi or less, 90 ppi or less, 80 ppi or less, 70 ppi or less, 60 ppi or less, 50 ppi or less, 40 ppi or less. As used herein, ppi (pore per inch) means a number of pores per inch.

As used herein, a pore number may be an average number of pores present on 1 inch line of width and length, measured precisely by W1-QA-14 (ASTM standard).

When the pore number per inch of sponge is larger than 130 ppi, the pore size is too small to control the flowability of a cosmetic composition and absorption/discharge of a cosmetic composition. When the pore number per inch of sponge is less than 30 ppi, the sponge may show poor supportability after a cosmetic composition is supported.

According to an embodiment, the layers of the single-body type sponge may have a different pore number. For example, the layer with a larger pore number per inch may have a pore number per inch of 100 ppi-130 ppi and the layer with a smaller pore number per inch may have a pore number per inch of 40 ppi-95 ppi.

As used herein, the term 'pore size' means an average diameter of the pores of a single-body type sponge.

As used herein, the single-body type sponge may have a pore size of 100-1500 μm, particularly 300-1500 μm, and more particularly 500-900 μm. For example, the pore size may be 100 μm or more, 200 μm or more, 300 μm or more, 400 μm or more, 500 μm or more, 600 μm or more, 700 μm or more, 800 μm or more, 900 μm or more, 1000 μm or more, 1100 μm or more, 1200 μm or more, 1300 μm or more, 1400 μm or more, or 1500 μm or less, 1400 μm or less, 1300 μm or less, 1200 μm or less, 1100 μm or less, 1000 or less, 900 μm or less, 800 μm or less, 700 or less, 600 or less, 500 or less, 400 μm or less, 300 μm or less, 200 μm or less. When the pore size is less than 100 μm, the single-body type sponge shows poor supporting capability and discharge capability. When the pore size is larger than 1500 μm, it may be difficult to control the flowability of a cosmetic composition and absorption/discharge of a cosmetic composition due to such an excessively large pore size.

As used herein, the term 'layer thickness' means the height of each layer of the single-body type sponge.

According to an embodiment, the thickness of each layer may be 0.05 mm-30 mm, particularly 0.1 mm-10 mm, and more particularly 0.5 mm-5.0 mm. For example, the thickness may be 0.05 mm or more, 1 mm or more, 5 mm or more, 10 mm or more, 15 mm or more, 20 mm or more, 25 mm or more, or 30 mm or less, 25 mm or less, 20 mm or less, 15 mm or less, 10 mm or less, 5 mm or less, 1 mm or less. When a sponge layer has a thickness within the above-defined range, it is suitable for providing a desired effect and it satisfies both the stability and safety as carrier. In addition, a thickness within the above-defined range is suitable in terms of cost efficiency. Particularly, when the layer thickness is excessively large, it is not possible to discharge a cosmetic composition well. When the layer thickness is excessively small, it is not possible to discharge a cosmetic composition homogeneously.

In addition, the layers of the single-body type sponge may have a different layer thickness. Particularly, a sponge layer with a smaller thickness may have a layer thickness of 0.05 mm-3 mm. Such a sponge layer with a smaller thickness may be formed by the pressurization. In addition, a sponge layer with a larger thickness may have a layer thickness larger than 0.5 mm and equal to or less than 10 mm.

According to an embodiment, when pressurizing the single-body type sponge, the layer subjected to pressurization may be pressurized by 0.5-3 times, preferably 1.1-2 times, and more preferably 1.5 times. According to an embodiment, the pressurized layer of the layers in the single-body type sponge may have a thickness corresponding to 0.5-60% of the total thickness of the single-body type sponge.

When the top layer of the layers in the single-body type sponge is excessively large, the effect provided by the lower layers is degraded, and thus the effect of introduction of a layered structure is degraded and the top layer may affect the discharge capability of a carrier more. Thus, it is important to control the thickness of the top layer. According to an embodiment, the top layer of the carrier for a cosmetic composition may have a thickness of 0.05 mm-3.0 mm, particularly 0.05 mm-2.8 mm, and more particularly 0.5 mm-2.5 mm.

According to an embodiment, the single-body type sponge may have an Asker hardness (i.e., hardness as determined by the Asker durometer type F) of 20-100, particularly 40-100. For example, the single-body type sponge may have an Asker hardness of 30 or more, 40 or more, 50 or more, 60 or more, 65 or more, 70 or more, 75 or more, 80 or more, 85 or more, 90 or more, 95 or more, or 100 or less, 95 or less, 90 or less, 85 or less, 80 or less, 75 or less, 65 or less, 60 or less, 50 or less, 40 or less, 30 or less. When the single-body type sponge has a hardness less than 20, it shows poor packability of a cosmetic composition and discharges an excessively large amount of cosmetic composition. When the single-body type sponge has a hardness larger than 100, it discharges an excessively small amount of cosmetic composition, resulting in degradation of a cosmetic effect.

According to an embodiment, foamed urethane, a kind of sponge, is not particularly limited but may include polyether-based foamed urethane (using ether polyol as main base), polyester-based foamed urethane and polycarbonate-based foamed urethane. Particularly, the foamed urethane may include polyether-based foamed urethane.

The polyether-based foamed urethane includes polyether-based dry foamed urethane and polyether-based wet foamed urethane, the polyester-based foamed urethane includes polyester-based dry foamed urethane and polyester-based wet foamed urethane, and the polycarbonate-based foamed urethane includes polycarbonate-based dry foamed urethane and polycarbonate-based wet foamed urethane.

According to an embodiment, the single-body type sponge may have a network structure. When the single-body type sponge has a network structure, it can support a cosmetic composition more homogeneously and show higher supporting efficiency, as compared to a non-network structure.

According to another embodiment, the layers of single-body type sponge may have a surface pattern formed thereon. Although there is no particular limitation in surface pattern, the surface pattern may be at least one of a three-dimensional surface embossed pattern and a pattern having a predetermined shape or style.

The cosmetic composition that may be applied to the carrier for a cosmetic composition disclosed herein may be in a liquid phase, viscous solid phase or a solid phase, including powder. Particularly, the cosmetic composition may be a liquid composition. According to an embodiment, the cosmetic composition may have a formulation of solution, emulsion, suspension, paste or jelly, but is not limited thereto.

According to another embodiment, the cosmetic composition may include at least one selected from an emulsion composition, water in oil (W/O) type composition or oil in water (O/W) type composition, oil dispersed composition, water dispersed composition and a solubilized composition.

The emulsion composition may have a viscosity ranging from low viscosity to high viscosity. Particularly, the emulsion composition may have a viscosity of 2,000 cps (centipoise) or more, and more particularly 4,000-80,000 cps. When the emulsion composition has a viscosity less than 2,000 cps, separation between an oil phase and an aqueous phase may occur right after preparing the emulsion cosmetic composition. Thus, it may be difficult to impregnate sponge foam homogeneously with such an emulsion cosmetic composition.

Herein, viscosity measurement may be carried out, for example, by using LVDV II+PRO with a spindle No. 63 at a spindle speed of 5 rpm.

According to an embodiment, the cosmetic composition may be formulated into make-up primer, make-up base, liquid or solid foundation, concealer, lipstick, lip gloss, powder, lip liner, eye liner, mascara, eyebrow, eye shadow, blusher, twin cake, UV protecting agent, lotion, cream or essence, but is not limited thereto.

In still another aspect, there is provided a cosmetic product including the carrier for a cosmetic composition in which a cosmetic composition is supported. Since the cosmetic product supports a cosmetic composition by the carrier for a cosmetic composition, the cosmetic composition may be packed well, the cosmetic composition may be supported homogeneously for a long time, the cosmetic composition may be discharged in an adequate amount when it is taken out of the carrier, and the cosmetic product may retain high durability for a long time. According to an embodiment, the cosmetic product may be provided in the form of a cosmetic container called briefly 'pact', which includes a lower part capable of receiving a carrier for a cosmetic composition and an upper lid part to which a mirror may be attached. According to another embodiment, the 'pact' may further include, in addition to the carrier, an applicator for taking the cosmetic composition supported by the carrier and applying it to the skin.

A conventional carrier for a cosmetic composition including sponge is disadvantageous in that it undergoes rapid drop in dischargeability of a cosmetic composition, once the cosmetic composition is taken out of the carrier in an amount of about 50% or more. On the contrary, the carrier for a cosmetic composition according to an embodiment of the present disclosure includes a single-body type sponge having a multi-layered structure. Thus, it is possible to control the dischargeability of a cosmetic composition more uniformly as compared to the conventional carrier for a cosmetic composition form the start of use to a time point where 50% or more of the cosmetic composition is used.

MODES FOR INVENTION

Hereinafter, the present disclosure will be described in detail through examples. However, the following examples are for illustrative purposes only and it will be apparent to those of ordinary skill in the art that the scope of the present disclosure is not limited by the examples.

Preparation Example

Preparation of W/O Type Emulsion Composition

A W/O type emulsion cosmetic composition is prepared according to the following Table 1 by using the conventional method.

TABLE 1

| | | Ingredients | Amount (wt %) |
|---|---|---|---|
| Oil phase ingredients | Oil ingredient | Ozokerite | 3.00 |
| | Oil ingredient | Dicaprylyl carbonate | 10.00 |
| | Preservative | Methyl paraben | 0.100 |
| | UV protecting agent | Octylmethoxy cinnamate | 7.000 |
| | UV protecting agent | Isoamyl-P-methoxy cinnamate | 2.000 |
| | Pigment | Disteardimonium hectorite | 1.50 |
| | Oil ingredient | Decamethylcyclopentasiloxane | 16.00 |
| | Emulsifier | Sorbitan sesquioleate | 1.000 |
| | Emulsifier | Lauryl PEG.PPG-18.18methicone | 1.500 |
| | Pigment | Polymethyl methacrylate | 5.00 |
| | Pigment | Titanium dioxide/aluminum hydroxide/stearic acid | 7.00 |
| Aqueous phase ingredients | | Water | To 100 |

TABLE 1-continued

| | Ingredients | Amount (wt %) |
|---|---|---|
| Moisturizer | Glycerin | 8.000 |
| Emulsion stabilizer | Salt | 1.00 |
| | Fragrance | 0.400 |
| | Total | 100.000 |

Example

Production and Evaluation of Carrier for Cosmetic Composition

First, the top portion of ether-based polyurethane is pressurized by hot pressing at 100-600° C. to provide a dry foamed urethane layer having a multi-layered structure. Next, the cosmetic composition obtained from Preparation Example is supported by the foamed urethane layer. Then, the carrier by which the cosmetic composition is supported is evaluated for whether or not the cosmetic composition is packed well (packability), whether or not the carrier supports the cosmetic composition homogeneously for a long time (supportability), whether or not an adequate amount of the cosmetic composition is discharged when the cosmetic composition is taken out of the carrier (dischargeability), and for the durability of the carrier after packing the cosmetic composition. The packability (packing capability) is determined by the time where 15 g of the cosmetic composition is packed, the dischargeability (discharge capability) is determined by the amount of the cosmetic composition when the cosmetic composition supported by the carrier is applied once by using puff. The supportability (supporting capability) is determined by the amount of the cosmetic composition retained in the foam when packing 15 g of the cosmetic composition is packed. The properties of each carrier for a cosmetic composition and the evaluation results are shown in the following Table 2.

TABLE 2

| | Single-layer dry polyurethane | Dry polyurethane having a layered structure |
|---|---|---|
| Description | Polyether-based dry foamed urethane | Polyether-based dry foamed urethane (bottom layer) + polyether-based dry foamed urethane (top layer) |
| ppi (pore per inch) | 85 ppi | 85 ppi |
| Density | 0.0288 g/cm³ | Top layer: 0.072 g/cm³ Bottom layer: 0.0288 g/cm³ |
| Packability | ⊚ | ⊚ |
| Supportability | ⊚ | ⊚ |
| Dischargeability | ○ | ⊚ |
| Durability after packing a composition | retains its initial state when stored for a long time | retains its initial state when stored for a long time |

As can be seen from the foregoing, when each layer of the carrier for a cosmetic composition has different properties, a cosmetic composition is packed well in the carrier, the carrier supports the cosmetic composition homogeneously for a long time, an adequate amount of cosmetic composition is discharged from the carrier, and the carrier shows high durability after packing a cosmetic composition.

Test Example 2

Evaluation for Carrier Quality Depending on Layer Thickness of Foamed Urethane

A carrier for a cosmetic composition having a layered structure including a foamed urethane layer is provided in the same manner as the above Example, except that the top portion of polyether-based foamed urethane (total thickness 13 mm) having a network structure with 85 ppi (pore per inch) is subjected to hot pressing so that the total thickness may be 10 mm (double layer). The cosmetic composition obtained from Preparation Example is supported in the carrier having a layered structure and evaluation is carried out. The results are shown in the following Table 3.

TABLE 3

Effect of Top Layer Having Different Thickness after Hot Pressing

| | Example 1 | Example 2 | Example 3 |
|---|---|---|---|
| ppi (pore per inch) | 85 ppi | 85 ppi | 85 ppi |
| Material | Polyether-based dry foamed urethane | Polyether-based dry foamed urethane | Polyether-based dry foamed urethane |
| Top layer thickness | 0.5 mm | 1 mm | 2.5 mm |
| Top layer density | 0.288 g/cm³ | 0.144 g/cm³ | 0.0576 g/cm³ |
| Packability | ○ | ⊚ | ○ |
| Supportability | ⊚ | ⊚ | ⊚ |
| Dischargeability | X | ⊚ | X |

As can be seen from the above results, the effect of a carrier for a cosmetic composition is varied when modifying the thickness of the top layer.

Test Example 3

Evaluation for Dischargeability

Figure 3:
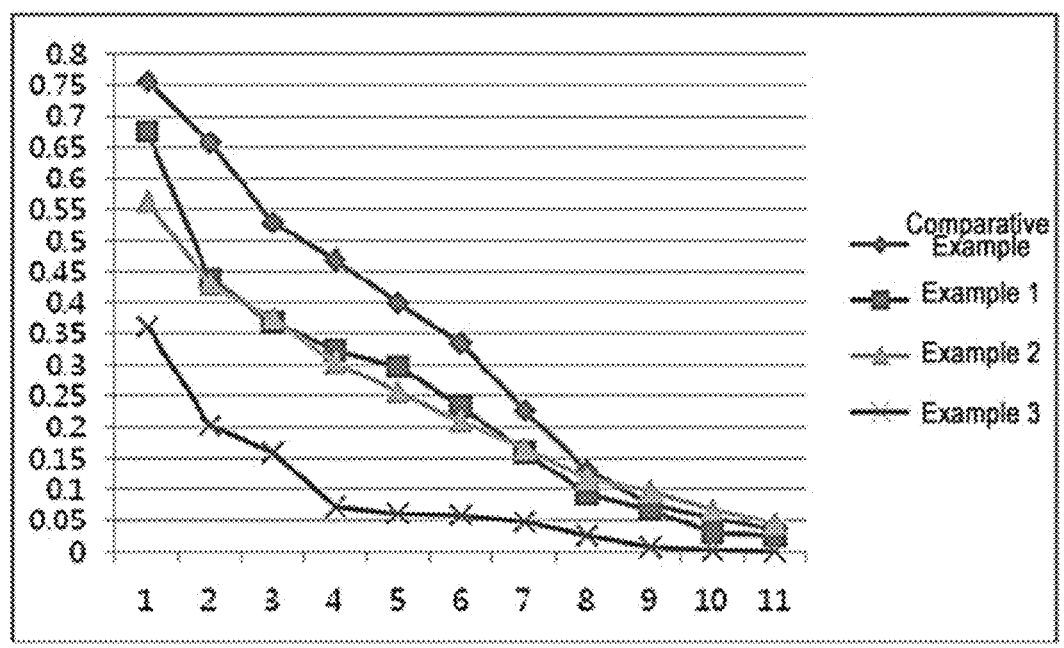
FIG. 3 is a graph illustrating the discharge capability of the single-body type carrier for a cosmetic composition according to an embodiment of the present disclosure.

A carrier for a cosmetic composition is prepared by using a single layer of the polyether-based foamed urethane as shown in Table 2 and used as Comparative Example. Each of Examples 1-3 of Test Example 2 is used as carrier for a cosmetic composition including double layers of polyether-based foamed urethane. The W/O type emulsion cosmetic composition obtained from Preparation Example is supported in each of Comparative Example and Examples 1-3 and the cosmetic composition is discharged. Then, the dischargeability is evaluated depending on number of discharge. The results are shown in the following Table 4 and FIG. 3.

In Table 4, the pay-off number (i.e. number of discharging a cosmetic composition with an applicator) means the number of taking the cosmetic composition out of the carrier, wherein the initial period corresponds to a pay-off number of 1-25, the middle period corresponds to a pay-off number of 35-55, and the later period corresponds to a pay-off number of 65-100. The dischargeability is expressed by the average pay-off amount for each period.

TABLE 4

Comparison of Dischargeability

| | Number | Comp. Ex. | Ex. 1 | Ex. 2 | Ex. 3 |
|---|---|---|---|---|---|
| Initial period | 1 | 0.7563 | 0.6761 | 0.5632 | 0.3622 |
| | 5 | 0.658 | 0.4383 | 0.4287 | 0.2033 |
| | 15 | 0.5292 | 0.3678 | 0.3753 | 0.16 |
| | 25 | 0.4703 | 0.3232 | 0.3028 | 0.0732 |
| Middle period | 35 | 0.4003 | 0.2963 | 0.2573 | 0.0621 |
| | 45 | 0.3337 | 0.2332 | 0.20821 | 0.0586 |
| | 55 | 0.2276 | 0.1602 | 0.1665 | 0.0467 |
| Later period | 65 | 0.1306 | 0.0933 | 0.1165 | 0.0254 |
| | 75 | 0.0764 | 0.0686 | 0.0965 | 0.0067 |
| | 85 | 0.0535 | 0.0298 | 0.0689 | 0.0023 |
| | 100 | 0.0352 | 0.0252 | 0.0459 | 0.0017 |

As can be seen from the above results, the carrier for a cosmetic composition including a single-body type sponge having a layered structure according to the present disclosure discharges a cosmetic composition homogeneously for a longer time as compared to the conventional carrier for a cosmetic composition including single-layer foam. Thus, it is possible for the users to take a predetermined amount of cosmetic composition out of the carrier for a long time during use.

INDUSTRIAL APPLICABILITY

The present disclosure relates to a carrier for a cosmetic composition by which the cosmetic composition is supported.

The invention claimed is:

1. A single-body carrier for a cosmetic composition comprising a single-body sponge, wherein the single-body sponge has a multilayered structure comprising at least two layers,
   wherein the single-body sponge comprises pores, and the layers of the sponge are different from each other in at least one of sponge density, pore number per unit volume (1 cm$^3$), pore size, and layer thickness,
   wherein the multilayered structure is formed by pressurization of a part of a single sponge and does not comprise binding or sealing of plurality of sponges.

2. The single-body carrier for a cosmetic composition according to claim 1, wherein the single-body sponge comprises pores, and has a layer controlled in at least one of density, pore number per unit volume (1 cm$^3$), pore size and layer thickness through the pressurization.

3. The single-body carrier for a cosmetic composition according to claim 2, wherein the pressurized layer in the layers of the single-body sponge has an average density of 0.025-0.5 g/cm$^3$.

4. The single-body carrier for a cosmetic composition according to claim 1, wherein the pore number per unit volume (1 cm$^3$) of the single-body sponge is 1000-600,000.

5. The single-body carrier for a cosmetic composition according to claim 1, wherein the number of pores contained per unit inch (1 inch) of the single-body sponge is 30 ppi-130 ppi (pore per inch).

6. The single-body carrier for a cosmetic composition according to claim 2, wherein the pore size of the single-body sponge, before pressurization, is 100-1500 μm on average.

7. The single-body carrier for a cosmetic composition according to claim 2, wherein the pressurized layer in the layers of the single-body sponge has a thickness corresponding to 0.5-60% based on the total thickness of the single-body sponge.

8. The single-body carrier for a cosmetic composition according to claim 1, wherein the single-body sponge has a network structure.

9. The single-body carrier for a cosmetic composition according to claim 1, wherein the layers of the single-body sponge has a surface pattern formed thereon.

10. A cosmetic product, comprising:
    the carrier for a cosmetic composition as defined in claim 1; and
    a cosmetic composition supported by the carrier.

11. The cosmetic product according to claim 10, wherein the cosmetic composition comprises a liquid composition.

12. The cosmetic product according to claim 10, wherein the cosmetic composition comprises at least one of an emulsion composition, water in oil (W/O) type composition or oil in water (O/W) type composition, oil dispersed composition, water dispersed composition and a solubilized composition.

* * * * *